United States Patent [19]

Stäahle et al.

[11] 4,438,118

[45] Mar. 20, 1984

[54] SUBSTITUTED IMIDAZO[1,2-a]PYRIMIDINES AND PHARMACEUTICAL COMPOSITIONS CONTAINING THEM

[75] Inventors: Helmut Stähle; Herbert Köppe; Werner Kummer, all of Ingelheim; Klaus Stockhaus, Bingen; Wolfram Gaida, Ingelheim; Wolfgang Hoefke, Wiesbaden, all of Fed. Rep. of Germany

[73] Assignee: Boehringer Ingelheim KG, Ingelheim am Rhein, Fed. Rep. of Germany

[21] Appl. No.: 389,284

[22] Filed: Jun. 17, 1982

[30] Foreign Application Priority Data

Jun. 24, 1981 [DE] Fed. Rep. of Germany ....... 3124718

[51] Int. Cl.$^3$ ............... C07D 487/00; A61K 31/505
[52] U.S. Cl. .................................... 424/251; 544/281
[58] Field of Search ..................... 544/281; 424/251

[56] References Cited

U.S. PATENT DOCUMENTS 3,769,288 10/1973 Stähle et al. ................. 544/281
3,816,422  6/1974 Stähle et al. ................. 544/281

FOREIGN PATENT DOCUMENTS 1513320  6/1978 United Kingdom ............. 548/337

Primary Examiner—Mary C. Lee
Assistant Examiner—S. A. Gibson
Attorney, Agent, or Firm—Hammond, Littell, Weissenberger & Dippert

[57] ABSTRACT

This invention relates to substituted imidazo[1,2-a]pyrimidines and non-toxic, pharmaceutically acceptable salts thereof. These compounds are useful in relieving pain and in treating hypertonia and coronary diseases.

14 Claims, No Drawings

SUBSTITUTED IMIDAZO[1,2-a]PYRIMIDINES AND PHARMACEUTICAL COMPOSITIONS CONTAINING THEM

This invention relates to novel substituted imidazo-[1,2-a]pyrimidines and non-toxic, pharmacologically acceptable acid addition salts thereof, to methods of preparing these compounds, to pharmaceutical compositions containing them as active ingredient, and to methods of using them as analgesics, as anti-hypertonia agents, and as cardiac and coronary therapeutic agents.

More particularly, the present invention relates to a novel class of compounds represented by the formula

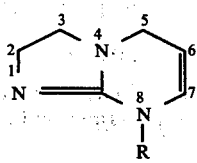 (I)

and non-toxic, pharmaceutically acceptable acid addition salts thereof. In Formula I, R represents a phenyl group which is mono-, di-, or trisubstituted by substituents selected from the group consisting of hydrogen, fluorine, chlorine and bromine atoms and methyl and trifluoromethyl groups, which substituents may be identical or different.

The acid addition salts comprise any desired non-toxic, pharmacologically acceptable salts formed with inorganic or organic acids. Examples of suitable such salts include hydrohalides such as hydrochlorides, sulfates, hydrogen sulfates, phosphates, hydrogen phosphates, tartrates, succinates, maleates, benzoates, acetates, propionates, lactates, ascorbinates, and the like.

The compounds of Formula I can be prepared in the following manner:

Method A

Compounds of the general formula

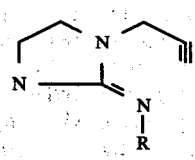 (II)

wherein R is as defined above, are thermally cyclized at temperatures of from about 60° to 180° C.

Method B

Compounds of the general formula

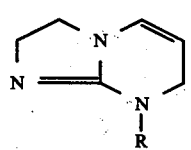 (III)

wherein R is as defined above, are isomerized in the presence of a strong base at temperatures of from about 40° to 60° C.

The thermal cyclization according to Method A is appropriately effected by heating the compounds of Formula II in the presence of a polar or apolar organic solvent to temperatures of from about 60° to 180° C. The particular temperatures depend on the reactivity of the compound of Formula II used.

Method A leads to the formation not only of the compounds of Formula I according to the invention but also to the isomeric compounds thereof of the general formula

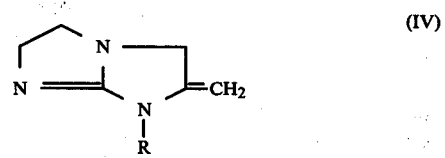 (IV)

wherein R is as defined above, which have to be separated. Since the isomers of Formulae I and IV differ significantly from one another in their pK values ($pK_I > pK_{IV}$), they are easy to separate from one another on the basis of this difference. By fractional extraction of the aqueous solution of a mixture of compounds of Formulae I and IV at increasing pH values, the less basic compounds of Formula IV can be extracted first, while the more strongly basic compounds of Formula I still remain in the aqueous solution.

The substances with a higher pK value, i.e., the compounds of Formula I, have been found to have a lower $R_F$ value than the isomeric compounds of Formula IV when investigated by thin layer chromatography (silica gel) in the following systems:

| System | Components | Component Reaction |
|---|---|---|
| A | toluene/dioxan/ethanol/concentrated ammonia | 50:40:5:5 |
| B | ethyl acetate/isopropanol/concentrated ammonia | 70:50:20 |
| C | sec.butanol/formic acid (85%)/H$_2$O | 75:15:10 |

After further alkalization of the aqueous solution, for example, with sodium hydroxide solution, to give a higher pH value, the compounds according to the invention may also be extracted in pure form and thereby isolated. The purity of the extracts can be checked by thin layer chromatography.

The process of isomerizing the compounds of Formula III (Method B) is suitably effected in polar aprotic solvents in the presence of a strong base, for example, potassium tert.butoxide, and at elevated temperature, for example, at a temperature of from about 50° to 60° C.

The structures of the new imidazo[1,2-a]pyrimidines of Formula I have been verified by $^1$H or $^{13}$C nuclear resonance and mass spectroscopy.

The starting compounds of Formula II are known and are described in, for example, German published application (DE-OS) No. 25 23 103, incorporated herein by reference. The starting compounds of Formula III can be prepared by thermal cyclization of 2-[N-(subst. phenyl)-N-propargylamino]-2-imidazolines at temperatures of from about 60° to 180° C.

The imidazo[1,2-a]pyrimidines of Formula I according to the invention can be converted into their non-toxic, pharmacologically acceptable acid addition salts in conventional manner. Acids suitable for salt formation include, for example, hydrochloric acid, hydrobromic acid, hydriodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methanesulfonic acid, 8-chlorotheophyllin, and the like.

The compounds of Formula I and the acid addition salts thereof have analgesic, hypotensive, and heart rate-reducing properties. The analgesic effect has been tested using the writhing test in the mouse. Moreover, measurement of blood pressure in rabbits to which these compounds were administered has shown that the compounds have a hypotensive activity. The effect on heart rate was investigated in spinal rats and in intact anesthetised rats. In view of these properties, the compounds of Formula I may be useful as medicaments for the treatment of pain, hypertonia, and coronary diseases.

The compounds of Formula I can be incorporated, optionally in combination with other active ingredients, into the usual pharmaceutical preparations such as tablets, coated tablets, capsules, powders, suppositories, or solutions. Such preparations may be produced with use of conventional pharmaceutical excipients, carriers, disintegrants, or lubricants or substances for obtaining delayed or sustained release. The single dose for adults is from about 0.1 to 80 mg (from about 0.0013 to 1.07 mg/kg), preferably, however, from about 1 to 30 mg (from about 0.013 to 0.40 mg/kg), 1 to 4 times daily.

Dependent upon the type and body weight of the patient to be treated, on the type and severity of the disease, on the type of preparation, and on the route of administration as well as on the period of interval over which the administration takes place, it may, however, be necessary to deviate from the above dosages. Thus, it may be sufficient in some cases to administer less than the above-mentioned amount of active ingredient or in some cases the amount may be exceeded. The optimum dosage and route of administration of the active ingredients which are necessary in each case can easily be determined by one skilled in the art.

The following examples are intended to illustrate the invention and should not be construed as limiting the invention thereto.

EXAMPLES

The following examples are representative preparations of compounds of Formula I.

EXAMPLE 1

8-(2,6-Dichlorophenyl)-2,3,5,8-tetrahydro-imidazo[1-2-a]pyrimidine

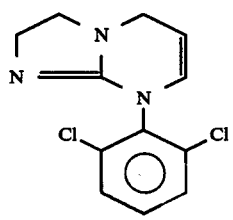

An amount of 5.4 gm of 1-propargyl-2-(2,6-dichlorophenylimino)-imidazolidine was refluxed in 40 ml of ethanol for ten hours, under stirring. The reaction mixture was then evaporated to dryness in vacuo. The residue was dissolved in 1 N hydrochloric acid, and the solution obtained was fractionally extracted with ether at increasing pH values (rendered alkaline with 2 N NaOH). The starting imidazolidine and an isomeric compound of Formula IV were separated by extraction at lower pH values (monitored by thin layer chromatography). As soon as the desired imidazo[1,2-a]pyrimidine was present in pure form in the aqueous phase, this was rendered further alkaline with 2 N sodium hydroxide solution, and the new compound was extracted with ether (the ether fractions being monitored by thin layer chromatography). After the ether was removed in vacuo, a yield of 1.1 gm was obtained, corresponding to 20.5% of theory.

Melting point: 156°-166° C.

The hydrobromide melted at 203°-204° C.

EXAMPLE 2

8-(2-Bromo-6-fluorophenyl)-2,3,5,8-tetrahydro-imidazo[1,2-a]pyrimidine

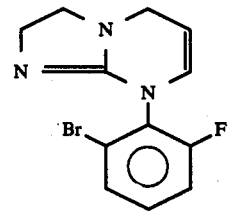

A quantity of 8.9 gm of 1-propargyl-2-(2-bromo-6-fluorophenylimino)-imidazolidine was refluxed in 60 ml of absolute ethanol for about 11 hours. The solvent was then removed in vacuo, and the remaining residue, consisting of the starting imidazolidine, 1-(2-bromo-6-fluorophenyl)-2,3,5,6-tetrahydro-2-methylene-1H-imidazo[1,2-a]imidazole, and the desired imidazo[1,2-a]pyrimidine, was dissolved in dilute 1 N hydrochloric acid.

Then, at increasing pH values (rendered alkaline with 2 N NaOH), the first two compounds mentioned were removed by fractional extraction with ethyl acetate. As soon as the aqueous solution contained only the new imidazo[1,2-a]pyrimidine (checked by thin layer chromatography), it was rendered further alkaline, and the new compound was extracted with ethyl acetate.

Yield: 0.9 gm (10.1% of theory) after evaporation in vacuo;

Melting point: 116°-120° C.

EXAMPLE 3

8-(2-Chloro-6-methylphenyl)-2,3,5,8-tetrahydro-imidazo[1,2-a]pyrimidine

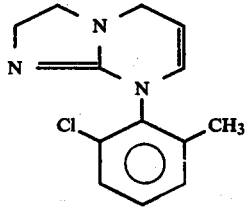

Six hundred twenty milligrams of 8-(2-chloro-6-methylphenyl)-2,3,7,8-tetrahydro-imidazo[1,2-a]pyrimidine were dissolved in 5 ml of dimethylsulfoxide, and 280 mg of potassium tert.butoxide were added to this solution, under stirring. The mixture was then heated to 50° to 60° C. for 48 hours. Subsequent to this time, some of the 2,3,7,8-tetrahydro-imidazo[1,2-a]pyrimidine added isomerized to form 2,3,5,8-tetrahydro-imidazo[1,2-a]pyrimidine. After the solvent was evaporated and the mixture of isomers was dissolved in dilute 1 N hydrochloric acid, as described in Examples 1 and 2, the isomers were separated by fractional extraction at increasing pH values (monitored by thin layer chromatography).

Melting point: 107°–113° C.

The compounds set forth in the following table were prepared by use of analogous procedures:

TABLE

| Example No. | R | Yield (% of theory) | M.p. (°C.) |
|---|---|---|---|
| 4 | 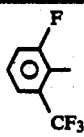 | 12.0 | 115–117° |
| 5 | 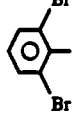 | 22.4 | 144–146° |
| 6 | 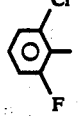 | 18.9 | 146–151° |
| 7 | 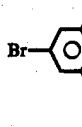 | 17.8 | 104–108° |
| 8 |  | 19.6 | 91–94° |
| 9 | 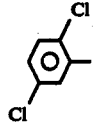 | 16.0 | 113–117° |
| 10 |  | 26.0 | 134–138° |
| 11 | 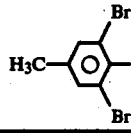 | 21.9 | 120–123° |

The following examples illustrate a few pharmaceutical dosage unit compositions comprising a compound of the invention as active ingredient.

EXAMPLE 12

Coated Tablets

Composition of one coated tablet:

| Component | Amount (mg) |
|---|---|
| Active ingredient according to the invention | 5 |
| Lactose | 65 |
| Corn starch | 130 |
| Sec. calcium phosphate | 40 |
| Soluble starch | 3 |
| Magnesium stearate | 3 |
| Colloidal silicic acid | 4 |
| Total | 250 |

Preparation

The active ingredient was mixed with some of the excipients, kneaded thoroughly with an aqueous solution of the soluble starch, and granulated in the usual way by means of a screen. The granulate was mixed with the remaining excipients and compressed to form tablet cores weighing 250 mg, which were then coated in the usual way with sugar, talc, and gum arabic.

EXAMPLE 13

Ampules

Composition of one ampule:

| Component | Amount |
|---|---|
| Active ingredient according to the invention | 1.0 mg |
| Sodium chloride | 18.0 mg |
| Distilled water | q.s. ad 2.0 ml |

Preparation

The active ingredient and sodium chloride were dissolved in water, and the resulting solution was transferred into glass ampules under a nitrogen atmosphere.

EXAMPLE 14

Drops

Composition of one vial:

| Component | Amount |
|---|---|
| Active ingredient according to the invention | 0.02 gm |
| Methyl p-hydroxybenzoate | 0.07 gm |
| Propyl p-hydroxybenzoate | 0.03 gm |
| Demineralized water | q.s. ad 100 ml |

Preparation

The active ingredient and preservatives were dissolved in demineralized water, and the resulting solution was filtered and transferred into vials each containing 100 ml.

Any one of the other compounds embraced by Formula I or a non-toxic, pharmacologically acceptable salt thereof with an inorganic or organic acid, may be substituted for the particular active ingredient employed in Examples 12 through 14. Likewise, the amount of the active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to other skilled in the art that the

We claim:
1. A compound of the formula

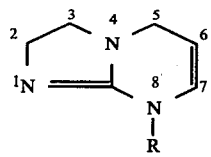

wherein R represents a phenyl group having from 1 to 3 substituents selected from the group consisting of hydrogen, fluorine, chlorine and bromine atoms and methyl and trifluoromethyl groups, the substituents being identical or different, or a non-toxic, pharmacologically acceptable acid addition salt thereof.

2. The compound of claim 1, wherein R is a 2,6-dichlorophenyl group.

3. The compound of claim 1, wherein R is a 2-bromo-6-fluorophenyl group.

4. The compound of claim 1, wherein R is a 2-chloro-6-methylphenyl group.

5. The compound of claim 1, wherein R is a 2-fluoro-6-trifluoromethylphenyl group.

6. The compound of claim 1, wherein R is a 2,6-dibromophenyl group.

7. The compound of claim 1, wherein R is a 2-chloro-6-fluorophenyl group.

8. The compound of claim 1, wherein R is a 2,4-dibromo-6-fluorophenyl group.

9. The compound of claim 1, wherein R is a 2,4-dichlorophenyl group.

10. The compound of claim 1, wherein R is a 2,5-dichlorophenyl group.

11. The compound of claim 1, wherein R is a 2,3-dichlorophenyl group.

12. The compound of claim 1, wherein R is a 2,6-dibromo-4-methylphenyl group.

13. A pharmaceutical dosage unit composition for relieving pain or treating hypertonia or coronary diseases consisting essentially of an inert pharmaceutical carrier and an effective amount of a compound of claim 1.

14. A method of relieving pain or treating hypertonia or coronary diseases in a host in need of such relief or treatment which comprises perorally, parenterally, or rectally administering to said host an effective pain relieving or hypertonia or coronary disease treating amount of a compound of claim 1.

* * * * *

UNITED STATES PATENT AND TRADEMARK OFFICE
CERTIFICATE OF CORRECTION

PATENT NO. : 4,438,118

DATED : March 20, 1984

INVENTOR(S) : HELMUT STÄHLE et al.

It is certified that error appears in the above-identified patent and that said Letters Patent are hereby corrected as shown below:

Title page, title line, "Stäahle et al." should read -- Stähle et al. --.

Column 3, lines 55 to 63, the structural formula should read:

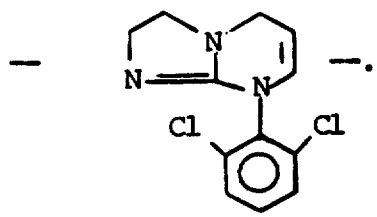

UNITED STATES PATENT AND TRADEMARK OFFICE
CERTIFICATE OF CORRECTION

PATENT NO. : 4,438,118

DATED : March 20, 1984

INVENTOR(S) : HELMUT STÄHLE et al.

It is certified that error appears in the above-identified patent and that said Letters Patent is hereby corrected as shown below:

Column 4, lines 57 to 64, the structural formula should read:

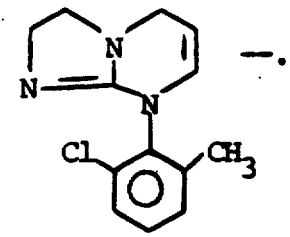

Signed and Sealed this

Sixth Day of November 1984

[SEAL]

Attest:

Attesting Officer

GERALD J. MOSSINGHOFF

Commissioner of Patents and Trademarks